United States Patent [19]
Anrep

[11] 3,955,286
[45] May 11, 1976

[54] METHOD OF AND INSTALLATION FOR TREATING VARIOUS OBJECTS BY MEANS OF MICROWAVES

[76] Inventor: René Anrep, 29 bis rue Carnot, Suresnes, Hauts-de-Seine, France

[22] Filed: Oct. 9, 1974

[21] Appl. No.: 513,462

[30] Foreign Application Priority Data
Oct. 12, 1973 France .............................. 73.36532

[52] U.S. Cl. .......................................... 34/1; 34/15; 21/54 R
[51] Int. Cl.² .......................................... F26B 3/34
[58] Field of Search .................. 34/1, 15, 233, 104, 34/105, 51; 219/10.55 R, 10.55 A; 21/54 R, 102 R

[56] References Cited
UNITED STATES PATENTS

| 2,132,303 | 10/1938 | Lathrop | 34/105 |
| 2,184,275 | 12/1939 | Baer | 34/15 |
| 2,309,290 | 1/1943 | Aksomitas | 34/104 |
| 2,613,480 | 10/1952 | Mongan, Jr. | 34/104 |
| 2,843,370 | 7/1958 | Engel et al. | 34/105 |
| 3,048,928 | 8/1962 | Copson et al. | 219/10.55 R |
| 3,737,608 | 6/1973 | Nagao et al. | 219/10.55 R |

*Primary Examiner*—Carroll B. Dority, Jr.
*Assistant Examiner*—Larry I. Schwartz
*Attorney, Agent, or Firm*—Watson, Cole, Grindle & Watson

[57] ABSTRACT

In a method of treating various objects, for example bottles or ampoules, by means of microwaves with a view to drying and/or sterilising them, the treatment is performed in a hermetic enclosure and the effect of the microwaves is combined with at least one abrupt variation of pressure within the enclosure, for example a lowering of the pressure followed by breaking of the vacuum. An installation for carrying out the method is also described.

7 Claims, 2 Drawing Figures

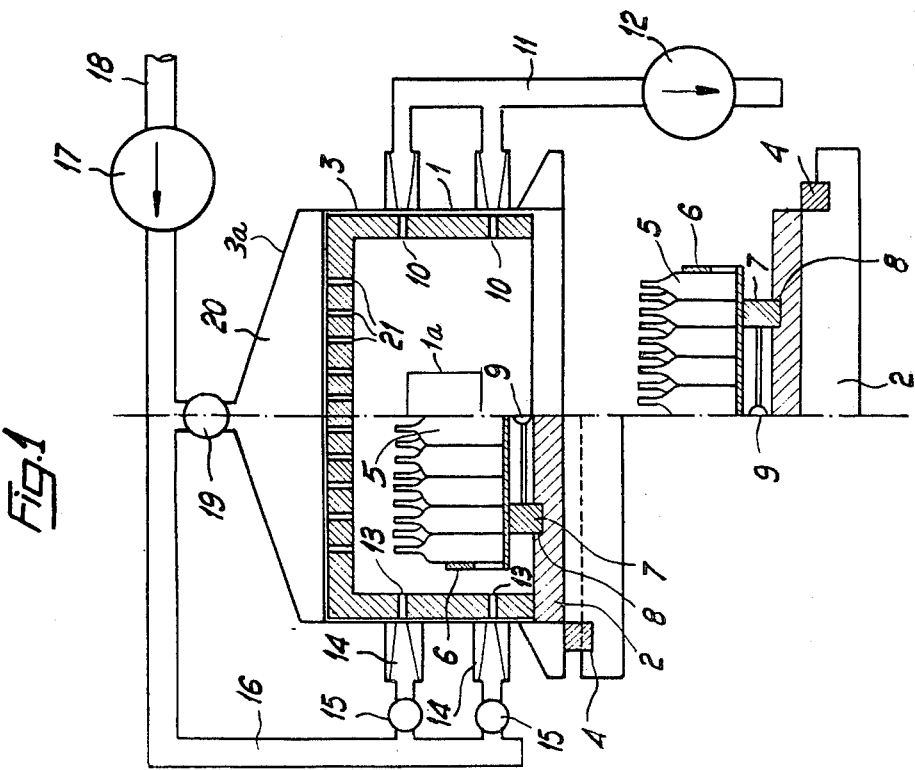

METHOD OF AND INSTALLATION FOR TREATING VARIOUS OBJECTS BY MEANS OF MICROWAVES

This invention relates to a method of, and an installation for, treating various objects by means of microwaves, that is to say electromagnetic waves in the centimetric or decimetric bonds, with a view to drying them, sterilising them or simultaneously drying and sterilising them.

The action of microwaves, combined with a ventilation, is known for drying various products, such as rubber, plastics, paints, ceramics, wood, food, textiles and paper, but, in order to remove the vapours produced by the action of the microwaves, it is necessary to employ very high ventilation flows.

Such high flows are difficult to achieve, having regard to the small dimensions with the inlet and outlet slits or orifices, formed in the walls of the cavities in which the microwaves act, must have if it is desired that the slits or orifices should not disturb the action of the microwaves.

In addition, the large consumption of energy required for the production of the large quantities of heated air or other gas, renders this method rather uneconomical and, moreover, when it is a question of treating complicated hollow articles, the removal of the vapours from the interior of the articles is a long and difficult operation.

The present invention aims to provide an improved method of, and an installation for, drying and/or sterilising various objects using microwaves in a manner which limits the quantities of air or other gas required and which accelerates the operation.

According to one aspect of the invention, a method of treating objects by means of microwaves with a view to drying and/or sterilising them, is characterised in that the treatment is performed in a hermetic enclosure and that the effect of the microwaves is combined with at least one abrupt variation of pressure within the enclosure, for example a lowering of the pressure followed by a rupture of the vacuum.

Preferably, during the course of the microwave treatment, several successive operations of lowering the pressure and of breaking the vacuum are performed, if necessary with blowing of gas into the enclosure at a pressure above atmospheric pressure, which permits total evacuation of vapour from the enclosure.

Whatever mode of carrying out the method is adopted, the non-evaporated portions remain colder since the evaporation under vacuum takes place at lower temperatures, which is an advantage, especially when it is necessary to avoid too great a heating of the treated objects.

The method is particularly effective as regards the drying and the sterilisation of receptacles such as ampoules, bottles and sachets. The power necessary for the production of the microwaves is smaller since the water or other liquid is evaporated at a lower temperature.

The operation is rapid, for example several minutes for drying 1000 ampoules of 2 milliliters capacity. The reason for this is that the ampoules remain cold, whereas it requires about one hour with normal heating followed by re-cooling.

The flow of air or other gas is smaller for example 100 to 200 liters per 1000 ampoules of 2 ml capacity instead of several thousands of liters in the known blowing methods. This leads to a more economical and more certain sterilisation of the drying air.

Since the method is performed in a hermetic enclosure, a very high degree of safety in a sterile medium can be achieved, and it is possible easily to control the sterility of the enclosure by removal, if necessary automatically, of air samples extracted when lowering the pressure in the said enclosure.

It is possible, in addition, to control automatically and simply the degree of humidity in the enclosure. It suffices, when the vacuum is established, to measure the degree of humidity of the air extracted from the enclosure and to do the same for the air introduced into the said enclosure.

These control possibilities make it possible to profit particularly well from the sterilising power of the microwaves.

According to a further aspect of the invention, an installation for carrying out the method of the invention comprises a hermetic enclosure associated with a source for producing microwaves, means for introducing a gas into the enclosure, and means for evacuating the gas.

The invention will now be described, by way of example, with reference to the accompanying drawing, in which FIG. 1 is a schematic transverse sectional view of an installation for performing the method according to the invention, and FIG. 2 is a graph illustrating one example of carrying out the method according to the invention.

The installation shown in FIG. 1 includes a tight enclosure 1 equipped with a device 10 for producing microwaves. These microwaves have a frequency of, for example from 2,425 to 2,475 megahertz and they are propagated perpendicular to the plane of the Figure.

The enclosure 1 includes two portions, namely a movable bottom 3a and a parallelepipedic cover 3, which can be connected together, via a suitable joint 4, to provide an assembly which substantially prevents leakage of gases and microwave power.

The numeral 5 designates hollow, open necked receptacles, for example ampoules, which are to be dried and/or sterilised. These receptacles are arranged side-by-side in a small box 6 which rests on supports 7 slidably mounted in grooves 8 in the bottom 2. A device such as a jack 9 allows reciprocation of the supports 7, and hence of the box and its contents, in the direction of propagation of the microwaves, for example with an amplitude of a little more than one quarter of the wavelength of the microwaves, which in this case means an amplitude of about 4 cm.

The enclosure 1 is pierced, in one of its sides parallel to the direction of propagation of the microwaves, with longitudinal slits 10 which may be connected, by means of a conduit 11, with a vacuum pump 12.

Slits or longitudinal orifices 13 are formed in the opposite side, some being situated at the level of the neck openings of the receptacles 5 and others at the level of the bottom of the receptacles. These slits 13 are connected to a conduit 16 by means of manifolds 14 provided with valves 15. The conduit 16 itself is connected to a blower 17 fed with air by a pipe 18, this air, if necessary, being suitably conditioned (dried and/or sterilised). The conduit 16 is also connected, via a valve 19, to a collector 20 which serves a plurality of holes 21 formed in the upper wall of the enclosure 1 substantially opposite the necks of the receptacles 5.

By means of such an arrangement of holes and slits it is possible to direct onto the receptacles three airflows in the manner described in my co-pending U.S. Pat. application No. 512,931, filed Oct. 7, 1974, which permits an economy in supplementary air.

In order to carry out the method of the invention, the procedure is as follows:

After having placed the box 6 containing the receptacles to be dried and sterilised in the enclosure 1, the latter is closed, a vacuum is established in the enclosure, and the microwave generator is started up.

These operations are illustrated by the graph of FIG. 2. In this Figure, the curve I represents the pressure in the enclosure 1, in millimeters of mercury (mm Hg), as a function of time expressed in seconds. The straight line II indicates as a function of time, the duration of the action of the microwaves.

An absolute pressure of from 20 to 40 mm Hg is obtained, for example in 20 seconds from the initial starting up of the vacuum pump 12 and in 15 seconds during normal running.

The vacuum is allowed to act for 10 seconds then it is interrupted by introducing previously filtered air through the slits 13 and the holes 21. This air, which may be heated, for example to a temperature of from 40° to 50°C may have an overpressure of, for example, from 200 to 400 mm Hg, with respect to atmospheric pressure. This operation also lasts 10 seconds and it is followed by a second pressure lowering in the course of which, also in 10 seconds, the absolute pressure of the enclosure is brought down to from 210 to 260 mm Hg, for example.

A new re-compression follows, for example of 10 seconds and up to the same pressure as previously, then a third pressure lowering operation in the course of which, also in 10 seconds, the absolute pressure of the enclosure is brought down to from 110 to 160 mm Hg.

Finally another re-compression, again up to 960–1160 mm Hg and in 10 seconds, is followed by a last pressure lowering operation, this time down to from 20 to 40 mm Hg, as in the case of the first pressure lowering operation. This final pressure lowering operation lasts for about 35 seconds. At this time the production of microwaves is stopped and the vacuum is broken. The entire operation has lasted approximately two minutes.

Of course, a single pressure lowering operation followed by one re-compression or one simple breaking of the vacuum may be sufficient. Also, depending on the particular case, it is possible to multiply these operations and to modify their duration as well as their intensity.

Again, it may be satisfatory to vary abruptly the pressure in the enclosure between atmospheric pressure and an overpressure of the order of for example several bars.

In order to permit a regular treatment by ensuring a good distribution of the microwaves over all the receptacles, it is possible to give the latter a reciprocating movement by means of the device 9. The enclosure may also be equipped with an agitator, for example a stirrer.

In addition to means used for increasing the sterilising power of the microwaves, a precise adjustment of the degree of humidity of the air introduced after the pressure lowering operations ensures the best conditions for sterilisation, for example in the case of certain spores which succumb more rapidly to a slightly humid atmosphere.

In a general manner, the invention makes it possible to obtain: a controlled drying with a desired residual humidity; if necessary, a sterilisation of objects already dried but requiring an atmosphere of controlled humidity; or a combination of these two operations.

The invention may be applied to the drying and/or to the sterilisation of a wide range of objects amongst which, in addition to the receptacles described above by way of example, may be mentioned powders, granules, pastes, or liquids.

What is claimed is:

1. A method for drying and sterilizing objects, comprising the steps of:
   a. placing said objects in a hermetic enclosure;
   b. providing a pre-selected pressure within said hermetic enclosure;
   c. directing electromagnetic radiation onto said objects; and
   d. repetitively decreasing and increasing the pressure within said hermetic enclosure while maintaining said electromagnetic radiation.

2. A method as in claim 1 wherein said electromagnetic radiation is applied constantly throughout the repetitive variations in pressure within the hermetic enclosure and the electromagnetic radiation is initiated after a predetermined stable pressure is obtained in the hermetic enclosure.

3. A method as in claim 1 wherein at least two variations of the pressure in the hermetic enclosure are provided.

4. A method as in claim 1 wherein the decrease in pressure is to a value below atmospheric pressure and the increase in pressure is obtained by admitting filtered gas into the hermetic enclosure.

5. A method as in claim 1 wherein the objects are given a reciprocating movement to obtain a distribution of the microwave radiation over all of the objects.

6. A method as in claim 1 in which the step of repetitively decreasing and increasing the pressure within the hermetic enclosure includes the steps of lowering the pressure to a range between 20 – 40 mm of Hg immediately after an initial pressure of approximately 760 mm of Hg is obtained in the hermetic enclosure, raising the pressure within the enclosure by admitting filtered air therein to a pressure in the range of 960 – 1160 mm Hg, decreasing the pressure within the hermetic enclosure to a range of 210 – 260 mm Hg, raising the pressure within the hermetic enclosure to a range of 960 – 1160 mm Hg, decreasing the pressure within the enclosure to a range of within 110 – 160 mm Hg, raising the pressure within the hermetic enclosure to a range of 960 – 1160 mm Hg, decreasing the pressure to a range of 20 – 40 mm Hg, and raising the pressure to the initial value of 760 mm Hg whereby the method is terminated.

7. The method as in claim 6 wherein the first decrease of pressure to 20 – 40 mm Hg is maintained for approximately ten seconds, the final step of reducing the pressure to 20 – 40 mm Hg is maintained for approximately 25 seconds, the intervening steps of increasing and decreasing said pressure are performed within ten second intervals and the electromagnetic radiation is terminated during the time when the pressure in the hermetic enclosure is last reduced to the range of 20 – 40 mm Hg.

* * * * *